(12) United States Patent
Blackstock et al.

(10) Patent No.: US 9,469,602 B2
(45) Date of Patent: Oct. 18, 2016

(54) REDOX-AUXILIARY CATALYSIS

(71) Applicant: The Board of Trustees of The University of Alabama, Tuscaloosa, AL (US)

(72) Inventors: Silas Blackstock, Tuscaloosa, AL (US); Lester Gray, Tuscaloosa, AL (US); Melody Kelley, Tuscaloosa, AL (US); Carl Saint-Louis, Tuscaloosa, AL (US)

(73) Assignee: The Board of Trustees of the University of Alabama, Tuscaloosa, AL (US)

( * ) Notice: Subject to any disclaimer, the term of this patent is extended or adjusted under 35 U.S.C. 154(b) by 0 days.

(21) Appl. No.: 14/530,150

(22) Filed: Oct. 31, 2014

(65) Prior Publication Data

US 2015/0133646 A1    May 14, 2015

Related U.S. Application Data

(60) Provisional application No. 61/898,716, filed on Nov. 1, 2013.

(51) Int. Cl.
| | |
|---|---|
| *C07F 17/02* | (2006.01) |
| *C07C 309/73* | (2006.01) |
| *C07C 245/08* | (2006.01) |
| *H01L 31/00* | (2006.01) |

(52) U.S. Cl.
CPC ........... *C07C 245/08* (2013.01); *C07C 309/73* (2013.01); *C07F 17/02* (2013.01); *H01L 31/00* (2013.01); *C07C 2102/42* (2013.01)

(58) Field of Classification Search
CPC .............................. C07F 17/02; C07C 309/73
See application file for complete search history.

(56) References Cited

PUBLICATIONS

Fraysse et al. (Eur. J. Inorg. Chem. 2000, 1581-1590).*
Heinze et al. (J Solid State Electrochem (1998) 2: 102-109).*
Sakano et al. (Eur. J. Inorg. Chem. 2005, 644-652).*
Chiu et al. (CAPLUS Abstract of: Journal of the Chinese Chemical Society (Taipei, Taiwan) (2006), 53(6), 1413-1418).*
Arlt et al. (Phys. Chem. Chem. Phys., 2010, 12, 13828-13834).*
Sun et al. (Journal of Polymer Science Part A: Polymer Chemistry 2012, 50, 3788-3796).*
Selby et al. (Chem. Mater. 2002, 14, 1685-1690).*
Gray et al. (OATD dissertation abstract showing publication date of 2012).*
Blackstock, Arylamine Redox Chemistry I Single Molecule Charge Writing in Films II Redox Auxiliary Catalysis, Presentation, University of St. Thomas, Oct. 5, 2012.
Blackstock, ACS Talk, Photo-Redox Isomerization of a Donor-Acceptor Norbornadience. A Solar Energy Transduction material, ACS National Meeting, Apr. 7, 2013, New Orleans, LA.
Chotsuwan et al., Single Molecule Charging by Atomic Force Microscopy, J. Am. Chem. Soc. 130:12556, 2008.
Dauben et al., Photochemical Transformations—VIII: The Isomerization of delta(2,6)-Bicyclo[2.2.1]heptadiene to quadricyclo[2.2.1.0(2,6).0(3.6)]heptane (Quadricyclane)3,Tetrahedron, 15:197, 1961.
Gassman et al., An Electrochemical "Switch" for Starting and Stopping the Energy-Releasing Conversion of Quadricyclanes to Norbornadienes, J. Org. Chem. 52:1337-1339, 1987.
Hammond et al., Photosensitized Cycloaddition Reactions, J. Am. Chem. Soc. 83:4674-4675, 1961.
Gray et al., Redox-Auxiliary Catalysis used to Develop New Solar Fuels, Mint Fall Review Poster, University of Alabama, Nov. 1, 2012, Tuscaloosa, AL.
Gray et al., The Application of Arylamines as Redox Auxiliaries Polar Crystals, and Organic Semiconductors, Dissertation, University of Alabama, Aug. 2013, Tuscaloosa, AL.
Louis et al. ACS Poster, Photo-Electro-Responsive Azo Compounds that Fold and Unfold, ACS National Meeting, Apr. 9, 2013, New Orleans, LA.
Selby et al., Preparation of a Redox-Gradient Dendrimer. Polyamines Designed for One-Way Electron Transfer and Charge Capture. J. Am. Chem. Soc., 120:12155, 1998.
Szulczewshi, Growth and characterization of poly(arylamine) thin films prepared by vapor deposition. J. Vac. Sci. Technol., A. 18:1875, 2000.

* cited by examiner

*Primary Examiner* — Robert Havlin
(74) *Attorney, Agent, or Firm* — Meunier Carlin & Curfman LLC

(57) ABSTRACT

Disclosed herein is a method of activating a compound for a chemical reaction comprising functionalizing a compound with a redox auxiliary group and oxidizing the redox auxiliary group that is bonded to the compound, thereby activating the compound, wherein the activated compound undergoes a chemical reaction to form a product and the oxidation of the redox auxiliary group is reversible. Methods of making and using these materials are also disclosed.

7 Claims, 12 Drawing Sheets

REDOX-AUXILIARY CATALYSIS

CROSS REFERENCES TO RELATED APPLICATION

This application claims benefit of U.S. Provisional Application No. 61/898,716, filed Nov. 1, 2013, which is hereby incorporated by reference in its entirety.

STATEMENT OF GOVERNMENT SUPPORT

This invention was made with government support under Grant No. NSF-DGE 1058257 awarded by the National Science Foundation. The government has certain rights in this invention

BACKGROUND

Redox catalysis is a rare but potentially valuable tool in organic synthesis and materials science which involves utilizing changes in oxidation state to catalyze a chemical transformation. While redox catalysis can demonstrate synthetic utility in specific cases, it is limited in scope and general applicability. This is mainly due to the requirement that, in order for a catalytic chain to be established, the product of a propagation step needs to be a stronger oxidant than the oxidized starting material. This is a demanding requirement that is not easily met. The methods and compositions disclosed herein address these and other needs.

SUMMARY

In accordance with the purposes of the disclosed materials, compounds, compositions, articles, devices, and methods, as embodied and broadly described herein, the disclosed subject matter, in one aspect, relates to compositions and methods for preparing and using the disclosed compositions. In more specific aspects, disclosed herein is a method of activating a compound for a chemical reaction comprising functionalizing a compound with a redox auxiliary group and oxidizing the redox auxiliary group that is bonded to the compound, thereby activating the compound, wherein the activated compound undergoes a chemical reaction to form a product and the oxidation of the redox auxiliary group is reversible. Methods of making and using these materials are also disclosed.

Also disclosed herein are compounds comprising a redox auxiliary moiety and a reactive moiety, wherein the redox auxiliary moiety is bonded to the reactive moiety, the oxidation of the redox auxiliary group activates the reactive moiety and catalyzes the conversion of the reactive moiety to a product, and the oxidation of the redox auxiliary moiety is reversible.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
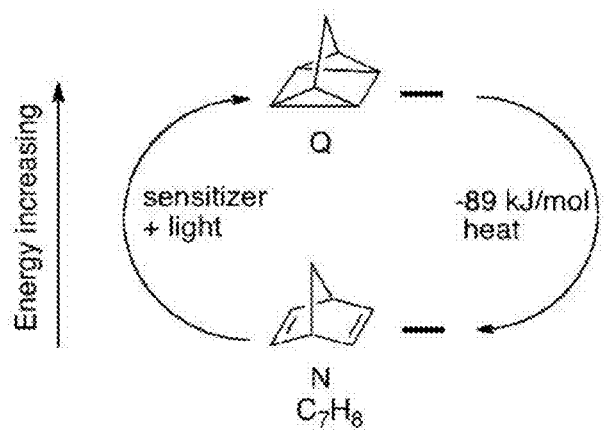
FIG. 1 shows the norbonadiene to quadricyclane photoconversion and the reverse thermal conversion.

The materials, compounds, compositions, articles, devices, and methods described herein may be understood more readily by reference to the following detailed description of specific aspects of the disclosed subject matter, figures and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Reference will now be made in detail to specific aspects of the disclosed materials, compounds, compositions, articles, and methods, examples of which are illustrated in the accompanying Examples and Figures.

CHEMICAL DEFINITIONS

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z_1$," "$Z_2$," "$Z_3$," etc. and "Y," are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, for example 1 to 3, 1 to 4, 1 to 5, 1 to 6, 1 to 7, 1 to 8, 1 to 9, 1 to 10, or 1 to 15 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms, for example, 2 to 5, 2 to 10, 2 to 15, or 2 to 20 carbon atoms, with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms, for example 2 to 5, 2 to 10, 2 to 15, or 2 to 20 carbon atoms, with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "carbonyl" as used herein is represented by the formula —C(O)$Z^1$ where $Z^1$ can be a hydrogen, hydroxyl, alkoxy, alkyl, halogenated alkyl, alkenyl, alkynyl, aryl, heteroaryl, cycloalkyl, cycloalkenyl, heterocycloalkyl, or heterocycloalkenyl group described above. Throughout this specification "C(O)" or "CO" is a short hand notation for C=O.

The term "aldehyde" as used herein is represented by the formula —C(O)H.

The terms "amine" or "amino" as used herein are represented by the formula —N$Z^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)N$Z^1Z^2$.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1$O$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1$C(O)$Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

When a substituent is described herein as being substituted, it can be substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein, unless stated to the contrary.

"$R^1$," "$R^2$," "$R^3$," "$R_n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Compounds

Disclosed herein are compounds comprising a redox auxiliary moiety and a reactive moiety, wherein the redox auxiliary moiety is bonded to the reactive moiety. In some embodiments, the oxidation of the redox auxiliary group can activate the reactive moiety and catalyze the conversion of the reactive moiety to a product.

A redox auxiliary moiety can be any group that is electroactive and stable in multiple oxidation states. Examples of redox auxiliary moieties include, but are not limited to, arylamines and metallocenes. In some examples, the oxidation of the redox auxiliary can be reversible. The redox auxiliary group, for example, can transfer its charge state to the compound it is bonded to.

In some cases, the redox auxiliary moiety can comprise an arylamine Arylamines can be stable radical carriers. In some examples, arylamines can have a high degree of thermal stability. Arylamines can be easily oxidized and they have a general lack of sensitivity to atmosphere. Examples of arylamines include, but are not limited to, diarylamines, triarylamines, p-phenylene-diamine, poly(arylamines), and combinations thereof. In some cases, the redox auxiliary can comprise a diarylamine. In some cases, the redox auxiliary moiety can comprise a triarylamine. In some cases, the redox auxiliary can comprise a poly(arylamine).

In some cases, the redox auxiliary moiety can comprise a metallocene. A metallocene comprises a metal and two cyclopentadienyl ligands coordinated in a sandwich structure. In some cases, the metallocene can comprise ferrocene.

In some examples, the reactive moiety can comprise an azo compound. As used herein, azo compounds are of the general structure R—N═N—R', wherein R and R' are independently selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted aryl, substituted or unsubstituted heteroaryl, alkoxy, hydroxy, nitrile, nitro, —C(O)$R_1$, —N$R_1R_2$, or —C(O)N$R_1R_2$; $R_1$ and $R_2$ are independently chosen from hydrogen, halogen, substituted or unsubstituted alkyl, substituted or unsubstituted alkenyl, substituted or unsubstituted alkynyl, substituted or unsubstituted aryl and substituted or unsubstituted heteroaryl. Azo compounds can undergo cis-trans isomerization, which can be used as a nanomechanical switch or a photoelectron responsive material. In some examples, the azo compound comprises an azobenzene compound. An azobenzene compound comprises two phenyl rings, which may be substituted or unsubstituted, linked by an N═N double bond. As a consequence of π-delocalization, aryl azo compounds can have vivid colors, therefore they are often used as dyes.

In some examples, the reactive moiety can comprise a bicyclic diene or a quadricyclane. In some examples, the reactive moiety can comprise norbornadiene. In some examples, the reactive moiety can comprise quadricyclane. Norbornadiene (N) can undergo photoconversion to a high-energy quadricyclane (Q) form via ~300 nm UV radiation. Quadricyclane's ring strain energy can be liberated in the form of heat (ΔH=−89 kJ/mol). The norbornadiene to quadricyclane photoreaction can convert light energy to chemical energy. The N/Q interconversions can be used to store solar energy in a recyclable solar energy fuel. The reversible N-Q cycle can involve mechanical motion and color change switching.

In some examples, the redox auxiliary moiety can be oxidized photochemically. In some examples, the redox auxiliary moiety can be oxidized electrochemically. In some examples, the oxidized redox auxiliary moiety can exchange an electron with a neutral redox auxiliary moiety to propagate electron transfer chain reaction to affect redox catalysis. In some examples, the redox auxiliary moiety can be bonded to the reactive moiety through a covalent bond.

Also disclosed herein are compounds of Formula (I)

wherein $X_1$ is chosen from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted aryl, substituted or unsubstituted heteroaryl, alkoxy, hydroxy, nitrile, nitro, —C(O)$R_1$, —N$R_1R_2$, or —C(O)N$R_1R_2$; $R_1$ and $R_2$ are independently chosen from hydrogen, halogen, substituted or unsubstituted alkyl, substituted or unsubstituted alkenyl, substituted or unsubstituted alkynyl, substituted or unsubstituted aryl and substituted or unsubstituted heteroaryl; and RA is a redox auxiliary group that can undergo reversible oxidation.

In some examples of Formula I, $X_1$ can comprise a substituted or unsubstituted aryl group. In some examples of Formula I, the redox auxiliary group can comprise an aryl group substituted with a redox auxiliary group.

In some examples of Formula I, the compound can comprise a compound defined by Formula (II)

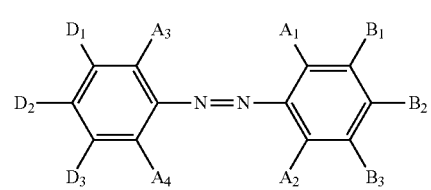

wherein $A_1$-$A_4$ are independently chosen from hydrogen, halogen, or any other sterically allowable group; $B_1$-$B_3$ are independently chosen from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted aryl, substituted or unsubstituted heteroaryl, alkoxy, hydroxy, nitrile, nitro, —C(O)$R_1$, —N$R_1R_2$, or —C(O)N$R_1R_2$; $D_1$-$D_3$ are independently chosen from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted aryl, substituted or unsubstituted heteroaryl, alkoxy, hydroxy, nitrile, nitro, —C(O)$R_1$, —N$R_1R_2$, or —C(O)NR$_1$R$_2$; R$_1$ and R$_2$ are independently chosen from hydrogen, halogen, substituted or unsubstituted C$_1$-C$_{24}$ alkyl, substituted or unsubstituted C$_2$-C$_{24}$ alkenyl, substituted or unsubstituted C$_2$-C$_{24}$ alkynyl, substituted or unsubstituted aryl and substituted or unsubstituted heteroaryl; with the proviso that at least one of D$_1$-D$_3$ is a redox auxiliary group that can undergo reversible oxidation.

In another embodiment of Formula II, none of D$_1$-D$_3$ is a redox auxiliary group, and A$_3$ and A$_4$ can be independently selected from hydrogen, halogen, substituted or unsubstituted C$_1$-C$_{24}$ alkyl, substituted or unsubstituted C$_2$-C$_{24}$ alkenyl, substituted or unsubstituted C$_2$-C$_{24}$ alkynyl, substituted or unsubstituted aryl, substituted or unsubstituted heteroaryl, alkoxy, hydroxy, nitrile, nitro, —C(O)R$_1$, —NR$_1$R$_2$, or —C(O)NR$_1$R$_2$; R$_1$ and R$_2$ are independently chosen from hydrogen, halogen, substituted or unsubstituted C$_1$-C$_{24}$ alkyl, substituted or unsubstituted C$_2$-C$_{24}$ alkenyl, substituted or unsubstituted C$_2$-C$_{24}$ alkynyl, substituted or unsubstituted aryl and substituted or unsubstituted heteroaryl; with the proviso that at least one of A$_3$ and A$_4$ is a redox auxiliary group that can undergo reversible oxidation.

In some examples of Formula II, the redox auxiliary group can comprise an arylamine. In some examples of Formula II, the arylamine can comprise a diarylamine. In some examples of Formula II, the redox auxiliary group can comprise a metallocene. In some examples of Formula II, the metallocene can comprise ferrocene.

In some examples of Formula II, A$_1$ is H. In some examples of Formula II, A$_2$ is H. In some examples of Formula II, A$_3$ is H. In some examples of Formula II, A$_4$ is H. In some examples of Formula II, A$_1$ and A$_2$ are H. In some examples of Formula II, A$_3$ and A$_4$ are H. In some examples of Formula II, A$_1$-A$_4$ are H.

In some examples of Formula II, at least one of B$_1$-B$_3$ comprises a substituted aryl group. In some examples of Formula II, B$_1$ is H. In some examples of Formula II, B$_3$ is H. In some examples of Formula II, B$_1$ and B$_3$ are H. In some examples of Formula II, B$_1$ and B$_3$ are H and B$_2$ comprises a substituted aryl group.

In some examples of Formula II, at least one of D$_1$-D$_3$ comprises an arylamine group. In some examples of Formula II, D$_1$ is H. In some examples of Formula II, D$_3$ is H. In some examples of Formula II, D$_1$ and D$_3$ are H. In some examples of Formula II, D$_1$ and D$_3$ are H and D$_2$ comprises an arylamine group.

In some examples of Formula II, the compound can comprise a compound defined by Formula III.

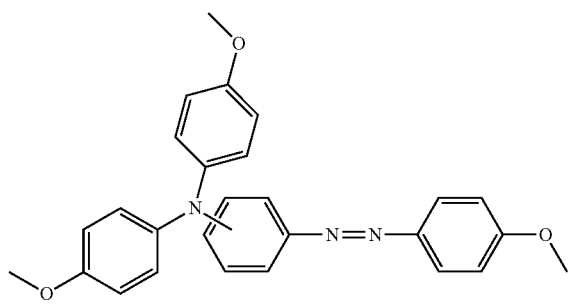

III

Also disclosed herein are compounds defined by Formula IV:

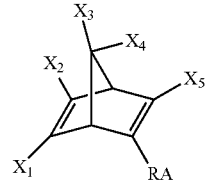

IV wherein X$_1$-X$_5$ are independently chosen from hydrogen, halogen, substituted or unsubstituted C$_1$-C$_{24}$ alkyl, substituted or unsubstituted C$_2$-C$_{24}$ alkenyl, substituted or unsubstituted C-C$_{24}$ alkynyl, substituted or unsubstituted aryl, substituted or unsubstituted heteroaryl, alkoxy, hydroxy, nitrile, nitro, —C(O)R$_1$, —NR$_1$R$_2$, or —C(O)NR$_1$R$_2$; R$_1$ and R$_2$ are independently chosen from hydrogen, halogen, substituted or unsubstituted C$_1$-C$_{24}$ alkyl, substituted or unsubstituted C$_2$-C$_{24}$ alkenyl, substituted or unsubstituted C$_2$-C$_{24}$ alkynyl, substituted or unsubstituted C$_1$-C$_{24}$ aryl and substituted or unsubstituted C$_1$-C$_{24}$ heteroaryl; and RA is a redox auxiliary group, with the proviso that if X$_1$-X$_4$ are each hydrogen and X$_5$ is a tosyl group, then RA is neither N,N-bis(4-methoxyphenyl)aniline nor N-phenyl-N,N,N-tris (4-methoxyphenyl)benzene-1,4-diamine.

In some examples of Formula IV, the compound comprises a compound defined by Formula V:

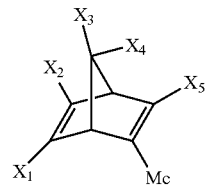

V wherein X$_1$-X$_5$ are independently chosen from hydrogen, halogen, substituted or unsubstituted C$_1$-C$_{24}$ alkyl, substituted or unsubstituted C$_2$-C$_{24}$ alkenyl, substituted or unsubstituted C-C$_{24}$ alkynyl, substituted or unsubstituted aryl, substituted or unsubstituted heteroaryl, alkoxy, hydroxy, nitrile, nitro, —C(O)R$_1$, —NR$_1$R$_2$, or —C(O)NR$_1$R$_2$; R$_1$ and R$_2$ are independently chosen from hydrogen, halogen, substituted or unsubstituted C$_1$-C$_{24}$ alkyl, substituted or unsubstituted C$_2$-C$_{24}$ alkenyl, substituted or unsubstituted C$_2$-C$_{24}$ alkynyl, substituted or unsubstituted C$_1$-C$_{24}$ aryl and substituted or unsubstituted C$_1$-C$_{24}$ heteroaryl; and Mc is a metallocene.

In some examples of Formula V, X$_1$ is H. In some examples of Formula V, X$_2$ is H. In some examples of Formula V, X$_3$ is H. In some examples of Formula V, X$_4$ is H. In some examples of Formula V, X$_1$ and X$_2$ are H. In some examples of Formula V, X$_3$ and X$_4$ are H. In some examples of Formula V, X$_1$-X$_4$ are H. In some examples of Formula V, X$_5$ is a tosyl group. In some examples of Formula V, the metallocene is ferrocene.

In some examples of Formula V, the compound comprises a compound defined by Formula VI:

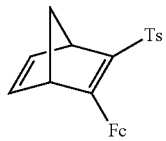

VI wherein Ts is a tosyl group and Fc is ferrocene.

In some examples, the compounds disclosed herein can be used as a solar fuel. A solar fuel is a fuel produced from sunlight, where light is used as an energy source and solar energy is transduced to chemical energy. Solar fuels are viewed as an alternative source of energy for replacing fossil fuels especially where storage is essential. Electricity can be produced directly from sunlight through photovoltaics, but this form of energy is rather inefficient to store. A solar fuel can be produced when and where sunlight is available, and stored and transported for later usage. Solar fuels can be produced via direct or indirect processes. Direct processes harness the energy in sunlight to produce a fuel without intermediary energy conversions. In contrast, indirect processes have solar energy converted to another form of energy first (such as biomass or electricity) that can then be used to produce a fuel. Indirect processes have been easier to implement but have the disadvantage of being less efficient than direct processes, since energy is wasted in the intermediary conversion.

Methods of Use

Disclosed herein are methods of activating a compound for a chemical reaction comprising functionalizing a compound with a redox auxiliary group and oxidizing the redox auxiliary group that is bonded to the compound, thereby activating the compound, wherein the activated compound undergoes a chemical reaction to form a product and the oxidation of the redox auxiliary group is reversible.

In some examples, the redox auxiliary group can comprise an arylamine Examples of arylamines include, but are not limited to, diarylamines, triarylamines, p-phenylenediamine, poly(arylamines), and combinations thereof. In some cases, the redox auxiliary group can comprise a diarylamine. In some cases, the redox auxiliary group can comprise a triarylamine. In some examples, the redox auxiliary group can comprise a poly(arylamine).

In some examples the redox auxiliary group can comprise a metallocene. In some examples the metallocene can comprise ferrocene.

In some examples, the reactive compound can comprise an azo compound. In some examples, the reactive compound can comprise an azobenzene compound In some examples, the compound can comprise a bicyclic diene or a quadricyclane.

In some examples, the compound can comprise norbornadiene. In some examples, the compound can comprise quadricyclane. Norbornadiene (N) can undergo photoconversion to a high-energy quadricyclane (Q) form via ~300 nm UV radiation. Quadricyclane's ring strain energy can be liberated in the form of heat ($\Delta H=-89$ kJ/mol). The norbornadiene to quadricyclane photoreaction can convert light energy to chemical energy. The N/Q interconversions can be used to store solar energy in a recyclable solar energy fuel. The reversible N-Q cycle can involve mechanical motion and color change switching.

In some examples, the redox auxiliary can be oxidized photochemically. In some examples, the redox auxiliary group can be oxidized electrochemically. In some examples, the oxidized redox auxiliary group can exchange an electron with a neutral redox auxiliary group to propagate electron transfer chain reaction to affect redox catalysis. In some examples, the reaction can be run at lower temperatures than if there was no redox auxiliary group attached to the reactive compound.

In some examples, the method further comprises the step of removing the redox auxiliary group from the product.

In some examples, the reaction can be an isomerization. In some examples, the isomerization can store or release energy. In some examples, the reaction can be a rearrangement reaction. In some examples, the reaction can be an electrocyclic reaction. In some examples, the reaction can be a photoelectrochemical reaction. In some examples the reaction can be a thermal reaction.

In some examples, the reaction can be used to store solar energy. In some examples, the reaction can be used as a mechanical switch. In some examples, the reaction can comprise a color change.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Example 1

Norbonadiene-Quadricyclane

Norbornadiene is a bicyclic, hydrocarbon and an organic compound. It has been intensively studied owing to its high reactivity and distinctive structural property of being a diene that can photoisomerize to a highly strained quadricyclane structure.

Quadricyclane is a strained, multi-cyclic hydrocarbon with potential uses as an additive for rocket propellants as well as in solar energy conversion. Quadricyclane is a highly strained molecule (78.7 kcal/mol). Isomerization of quadricyclane proceeds slowly at ambient temperatures without the use of a catalyst.

Norbornadiene (N) undergoes photoconversion to a high-energy quadricyclane form (Q), as shown in FIG. 1. The norbornadiene to quadricyclane photoreaction converts light energy to chemical energy. If the N-to-Q and Q-to-N reactions can be harnessed, then the N/Q interconversions can be used to store solar energy in a recyclable solar energy fuel. The reversible N-Q cycle involved mechanical motion and color change switching.

Figure 2:
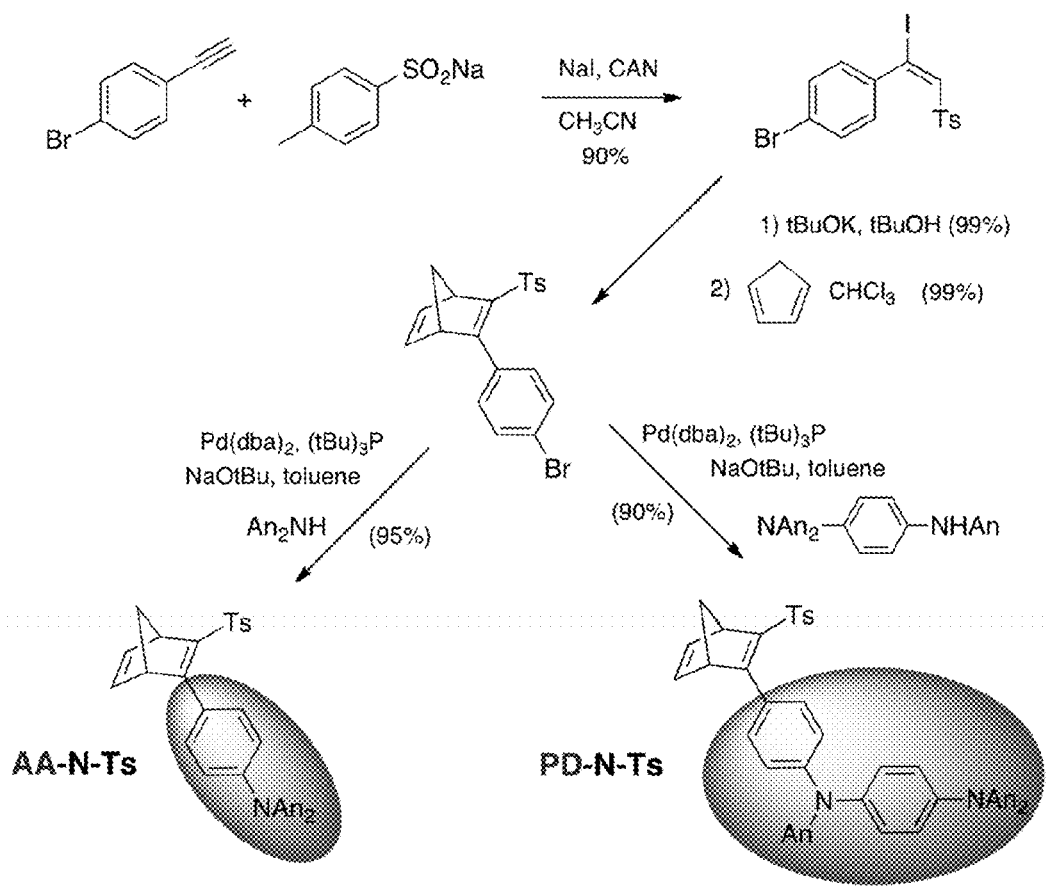
FIG. 2 shows the reaction schemes for synthesizing AA-N-Ts and PD-N-Ts.

Two redox-auxiliary appended norbornadienes (AA-N-Ts and PD-N-Ts) were synthesized according to the reaction scheme in FIG. 2, wherein "An" stands for anisole.

Figure 3:
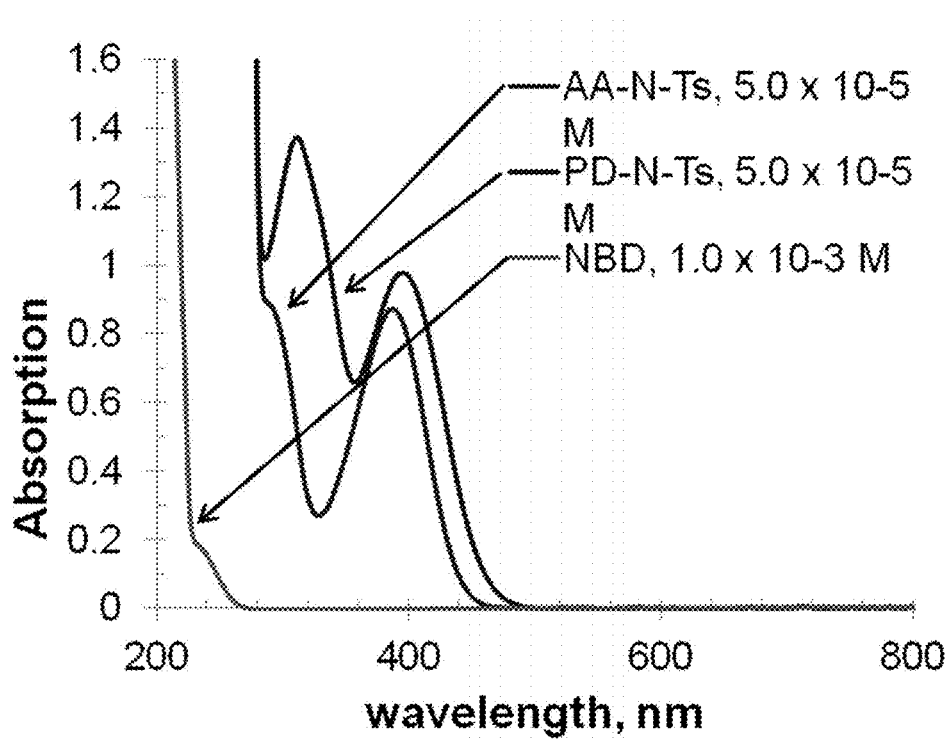
FIG. 3 shows the optical spectra of norbonadiene, AA-N-Ts and PD-N-Ts.

The optical spectra of AA-N-Ts, PD-N-Ts and native norbornadiene are shown in FIG. 3. The native norbornadiene shows no appreciable absorption above 250 nm. The AA-N-Ts compound shows a distinct band at about 400 nm, whereas the PD-N-Ts shows two distinct bands at about 320 nm and 400 nm. The 1,2-donor/acceptor substitution gives a large red shift of the optical absorptions, moving the HOMO to LUMO transition into the visible region.

Figure 4:
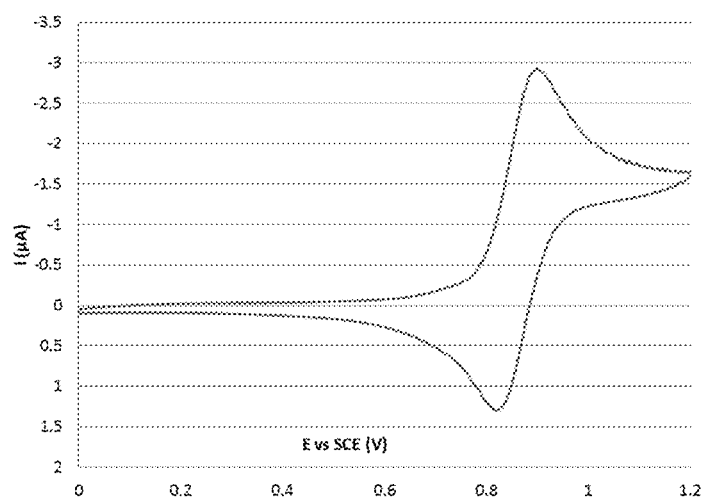
FIG. 4 shows the cyclic voltammogram of AA-N-Ts.
Figure 5:
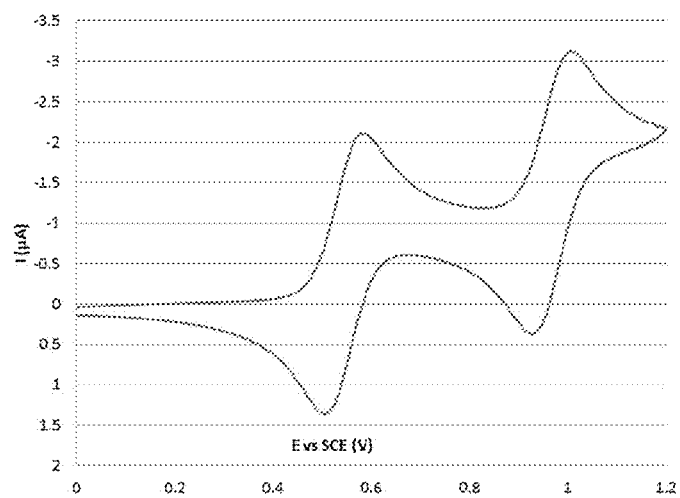
FIG. 5 shows the cyclic voltammogram of PD-N-Ts.

The cyclic voltammograms of AA-N-Ts and PD-N-Ts are shown in FIG. 4 and FIG. 5, respectively. AA-N-Ts displays one peak at E=0.86, while PD-N-Ts displays two peaks at e=0/55 and E=0.95, all as measured against a saturated calomel electrode. In both cases, it is clear that the oxidation(s) of the redox-auxiliary group is reversible.

Figure 6:
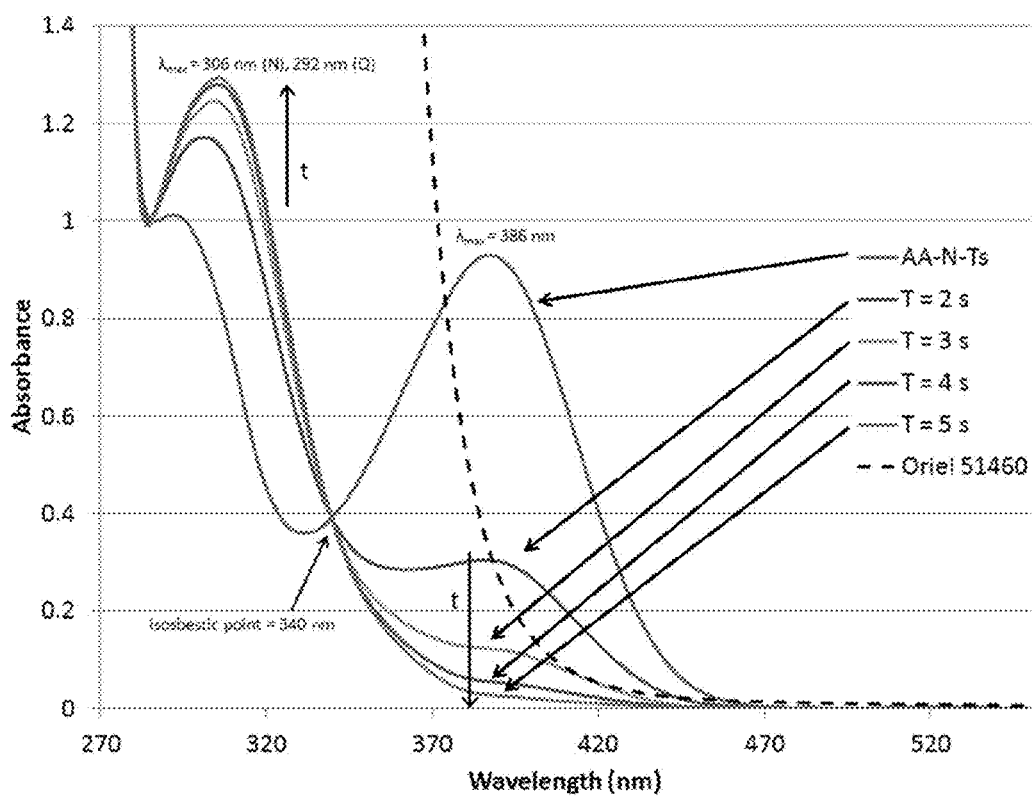
FIG. 6 shows the photoconversion of AA-N-Ts to AA-Q-Ts over time with irradiation from an arc lamp with a >400 nm cutoff filter.

The conversion of the AA-N-Ts compound to its relative quadricyclane form (AA-Q-Ts) upon addition of intense light from an arc lamp and benzene was monitored spectroscopically, as shown in FIG. 6. In this case, a >400 nm cutoff filter (Oriel 51460) was used, establishing the long wavelength band as photoactive for the isomerization. The initial AA-N-Ts compound shows a large peak at 386 nm that decreases in intensity over time with the addition of light and benzene, indicating the conversion to the AA-Q-Ts form. Concomitantly, there is an increase in the intensity of a band at about 300 nm corresponding to the increase in the amount of AA-Q-Ts. Within 5 seconds, appreciably all of the AA-N-Ts has been converted to AA-Q-Ts.

Figure 7:
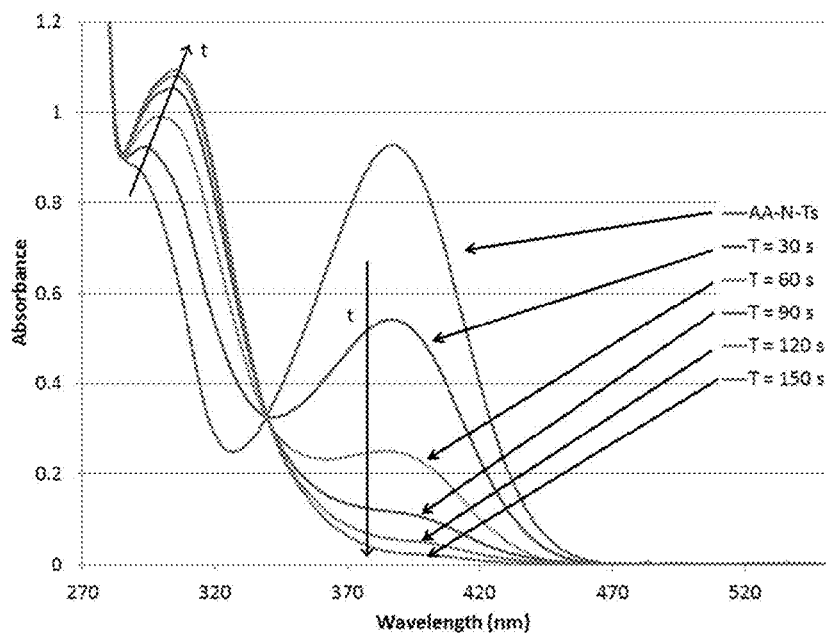
FIG. 7 shows the photoconversion of AA-N-Ts to AA-Q-Ts over time with irradiation from indirect sunlight.

The conversion of the AA-N-Ts compound to its relative quadricyclane form (AA-Q-Ts) upon irradiation with indirect, low intensity solar light and with the addition of benzene was monitored spectroscopically, as shown in FIG. 7. The initial AA-N-Ts compound shows a large peak at 386 nm that decreases in intensity over time with the addition of light and benzene, indicating the conversion to the AA-Q-Ts form. Concomitantly, there is an increase in the intensity of a band at about 300 nm corresponding to the increase in the amount of AA-Q-Ts. Under these conditions, the conversion progresses slower and appreciably all of the AA-N-Ts has been converted to AA-Q-Ts after about 120 s.

Figure 8:
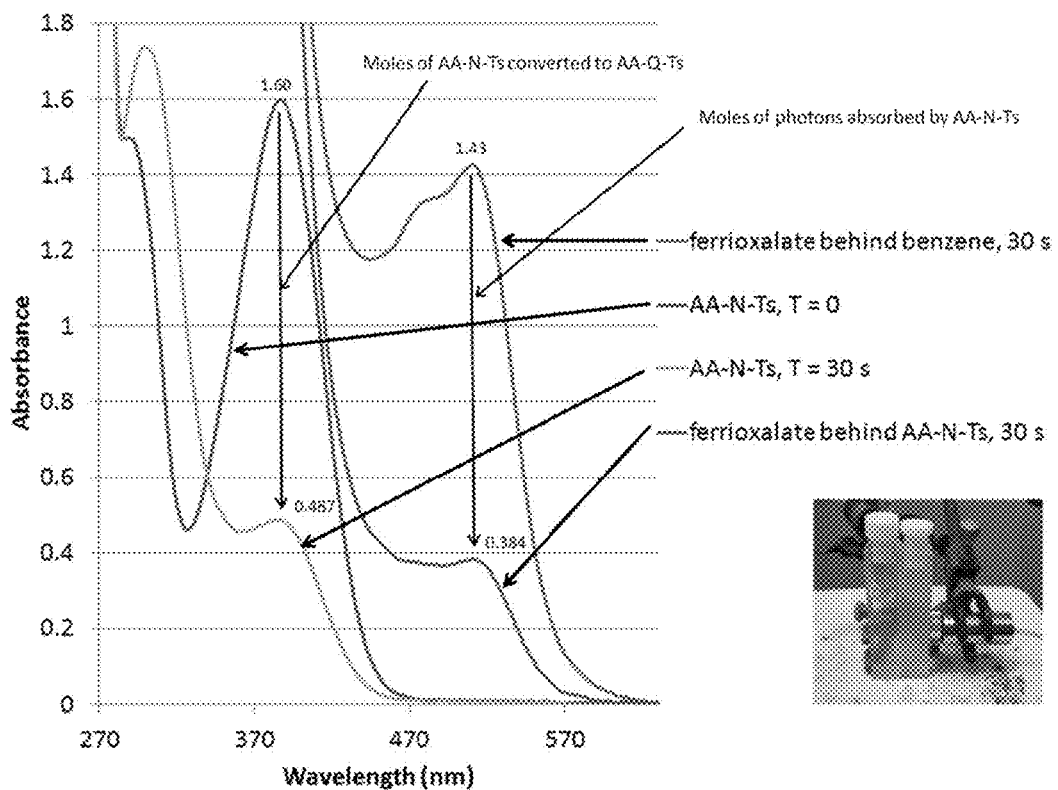
FIG. 8 shows the quantum efficiency of the AA-N-Ts to AA-Q-Ts conversion.

The quantum yield of the conversion was found to be 0.60±0.02, as shown in FIG. 8, meaning 60% of the absorbed photons result in the N to Q conversion of the compound.

Figure 9:
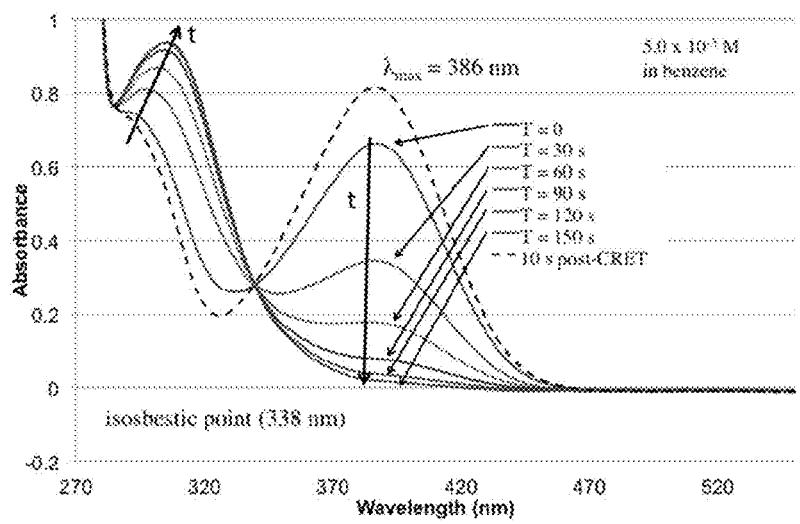
FIG. 9 shows the conversion of AA-Q-Ts back to AA-N-Ts after the addition of CRET.

Upon addition of a chemical oxidant, specifically a cation radical electron transfer reagent (CRET), the AA-Q-Ts converts back to the AA-N-Ts form in 10 seconds or less, as shown in FIG. 9.

Example 2

Azobenzenes

Azobenzenes undergo reversible photo-isomerization between extended and contracted states. However, this isomerization requires fairly high energy light (UV or blue light) under normal circumstances and backconversion is often inefficient or not possible photochemically.

Figure 10:
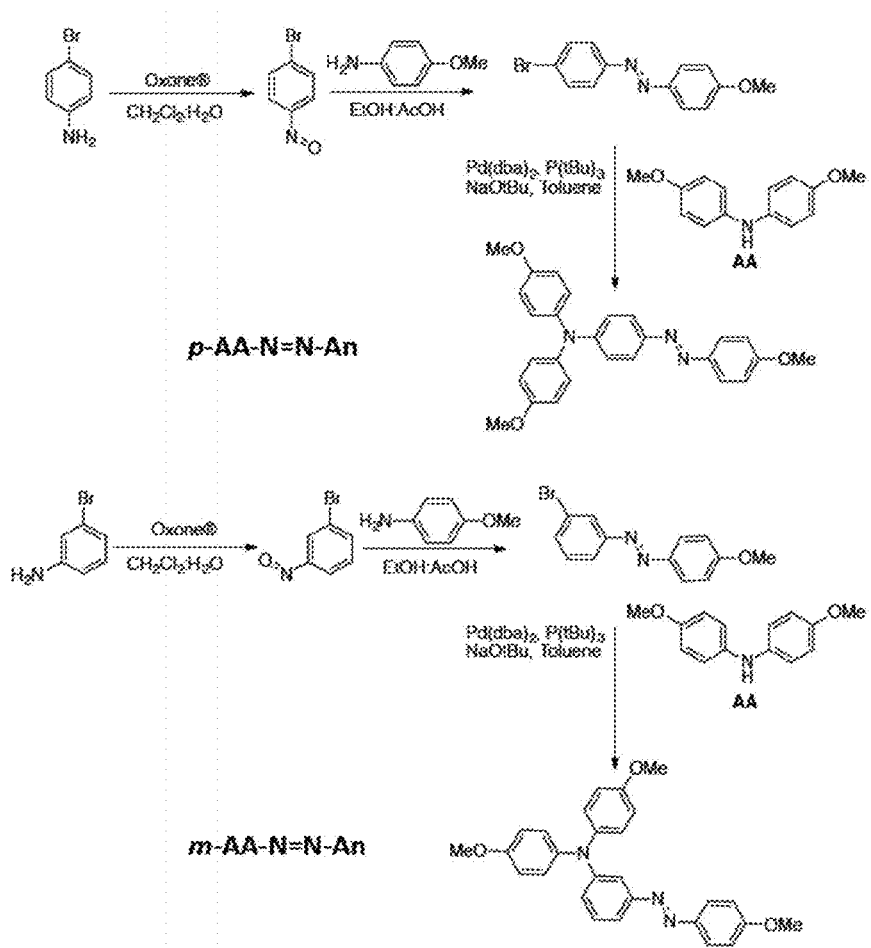
FIG. 10 shows the reaction schemes for synthesizing the para and meta redox auxiliary appended azobenzenes.

Redox auxiliaries were appended to the azo-benzene structure at different positions to evaluate their effects. The reaction schemes for both are shown in FIG. 10.

Figure 11:
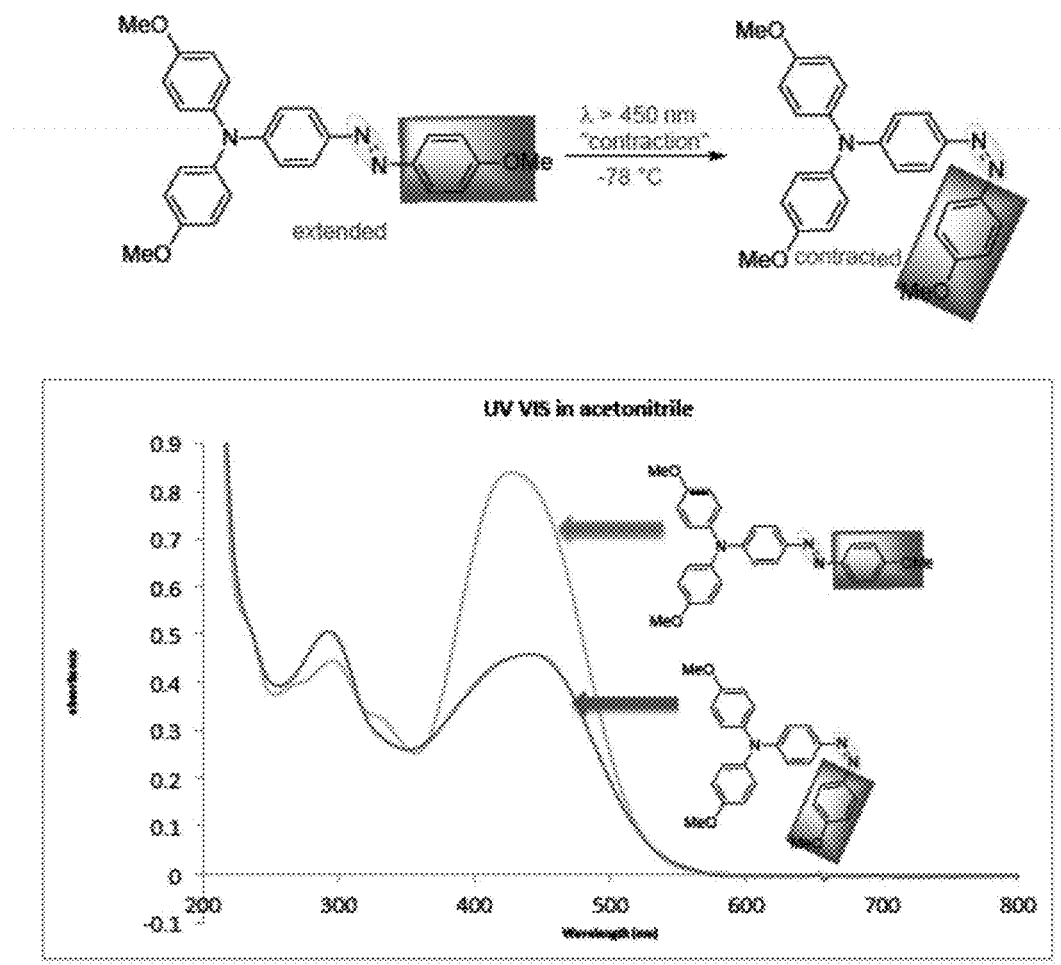
FIG. 11 shows the optical spectra of the extended and contracted forms of the p-AA-N=N-An.
Figure 12:
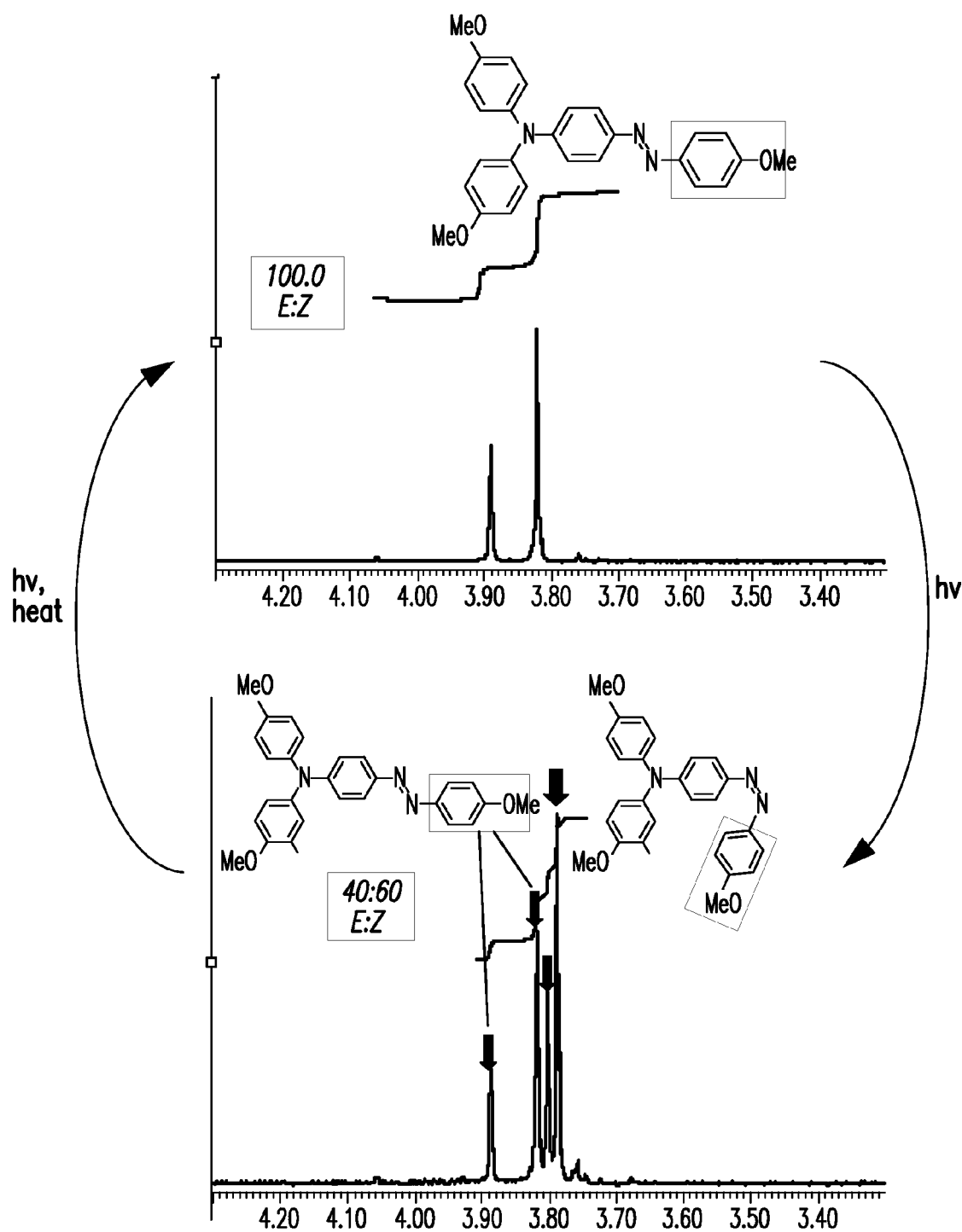
FIG. 12 shows the change in the methyl H NMR signals between the extended and contracted forms of the p-AA-N=N-An.
Figure 13:
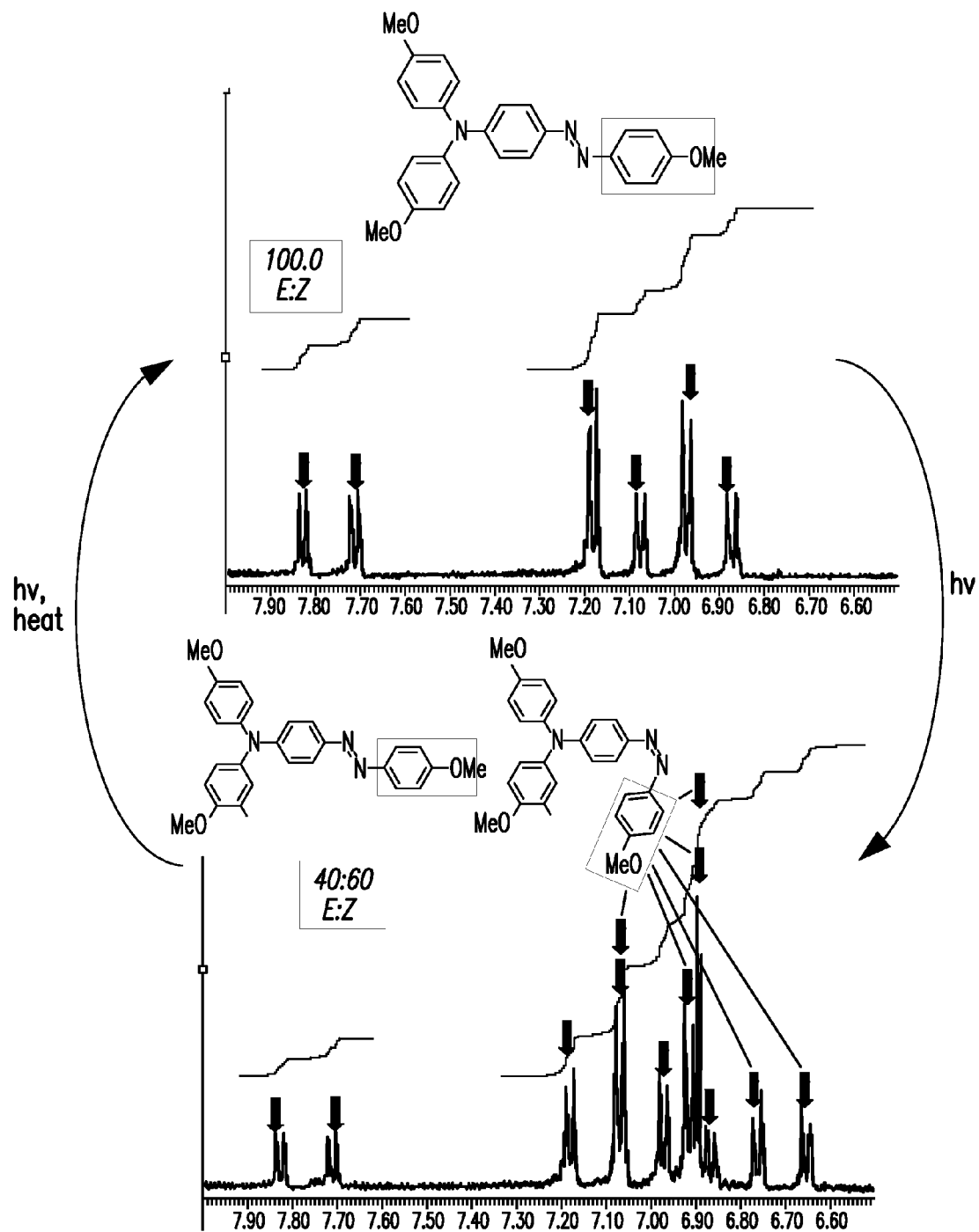
FIG. 13 shows the change in the aromatic H NMR signals between the extended and contracted forms of the p-AA-N=N-An.
Figure 14:
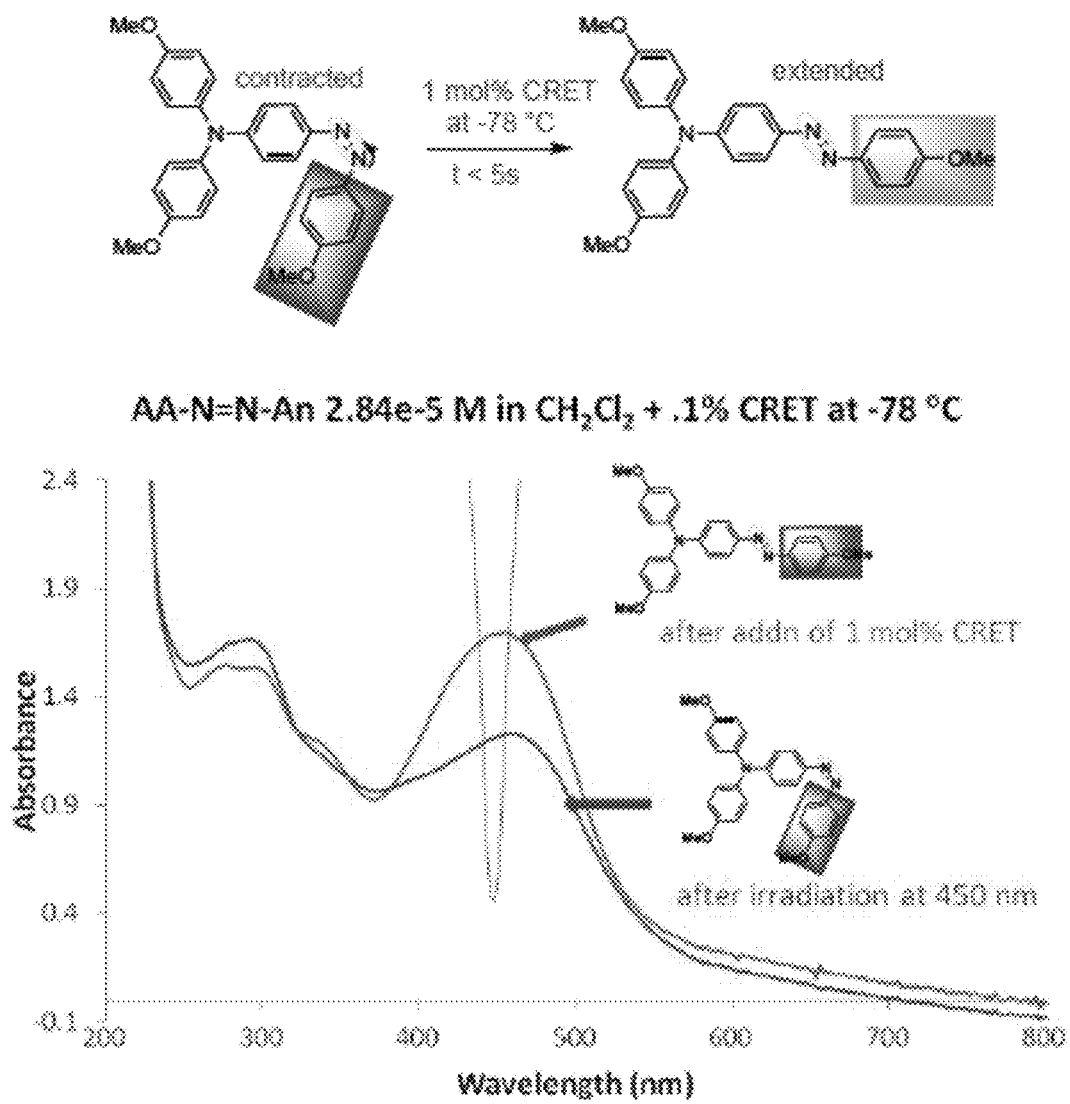
FIG. 14 shows the unfolding of the p-AA-N=N-An upon addition of CRET.

For the p-AA-N=N-An, conversion from the extended to the contracted state ("folding") was achieved with light of wavelengths longer than 450 nm, as shown in FIG. 11. The folding was also confirmed by observing changes in the H NMR signals of the methyl group (FIG. 12) and aromatic groups (FIG. 13). Transition from the contracted state to the extended state ("unfolding") was achieved through the addition of a small amount of CRET (FIG. 14).

Figure 15:
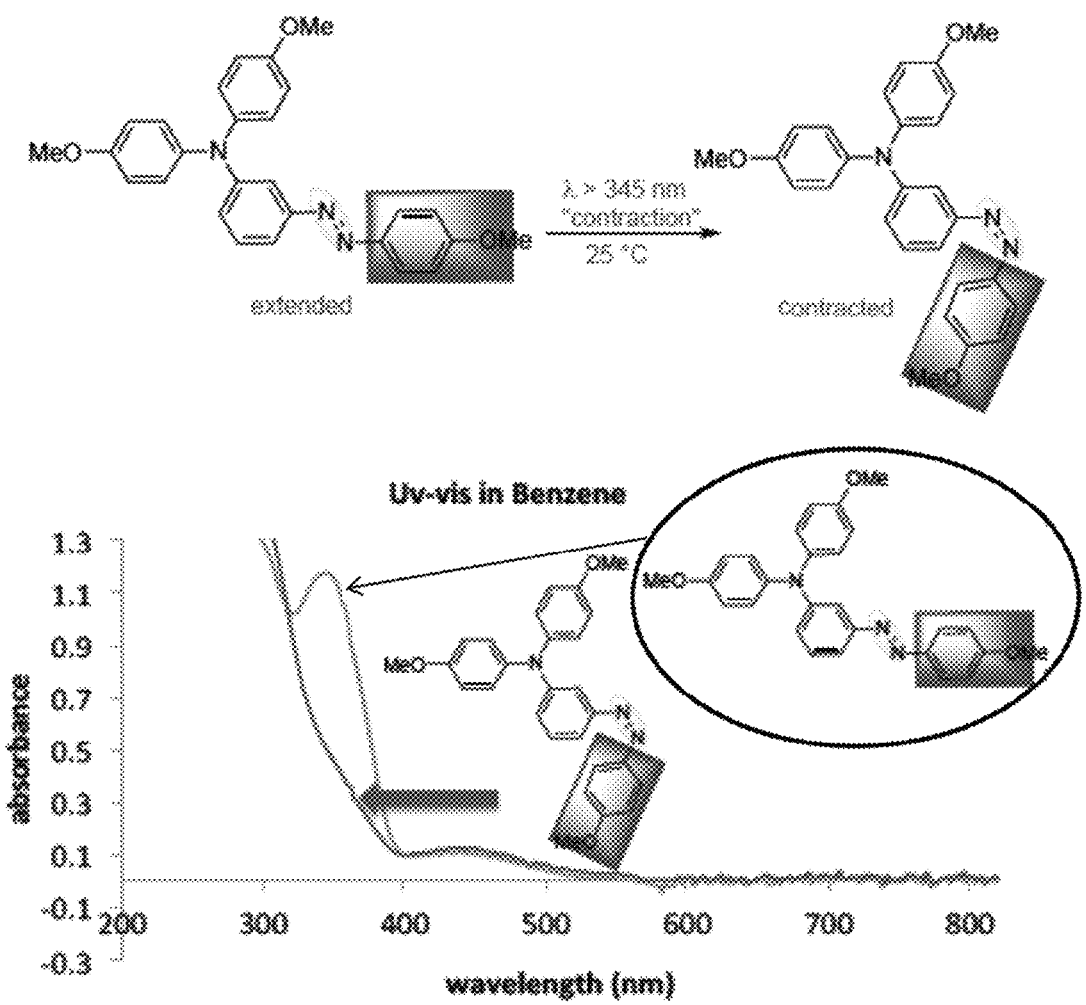
FIG. 15 shows the optical spectra of the extended and contracted forms of the m-AA-N=N-An.
Figure 16:
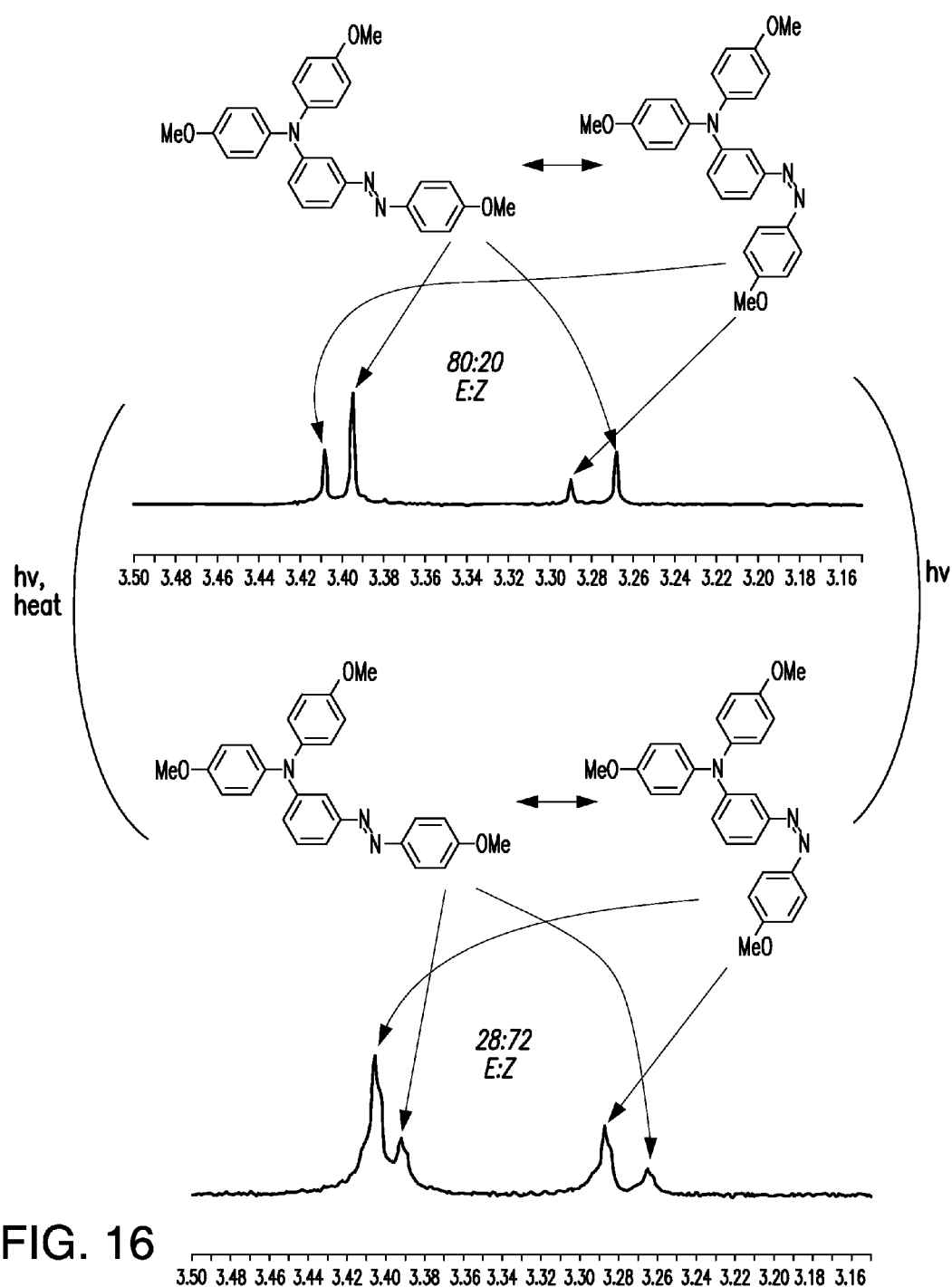
FIG. 16 shows the change in the methyl H NMR signals between the extended and contracted forms of the m-AA-N=N-An.
Figure 17:
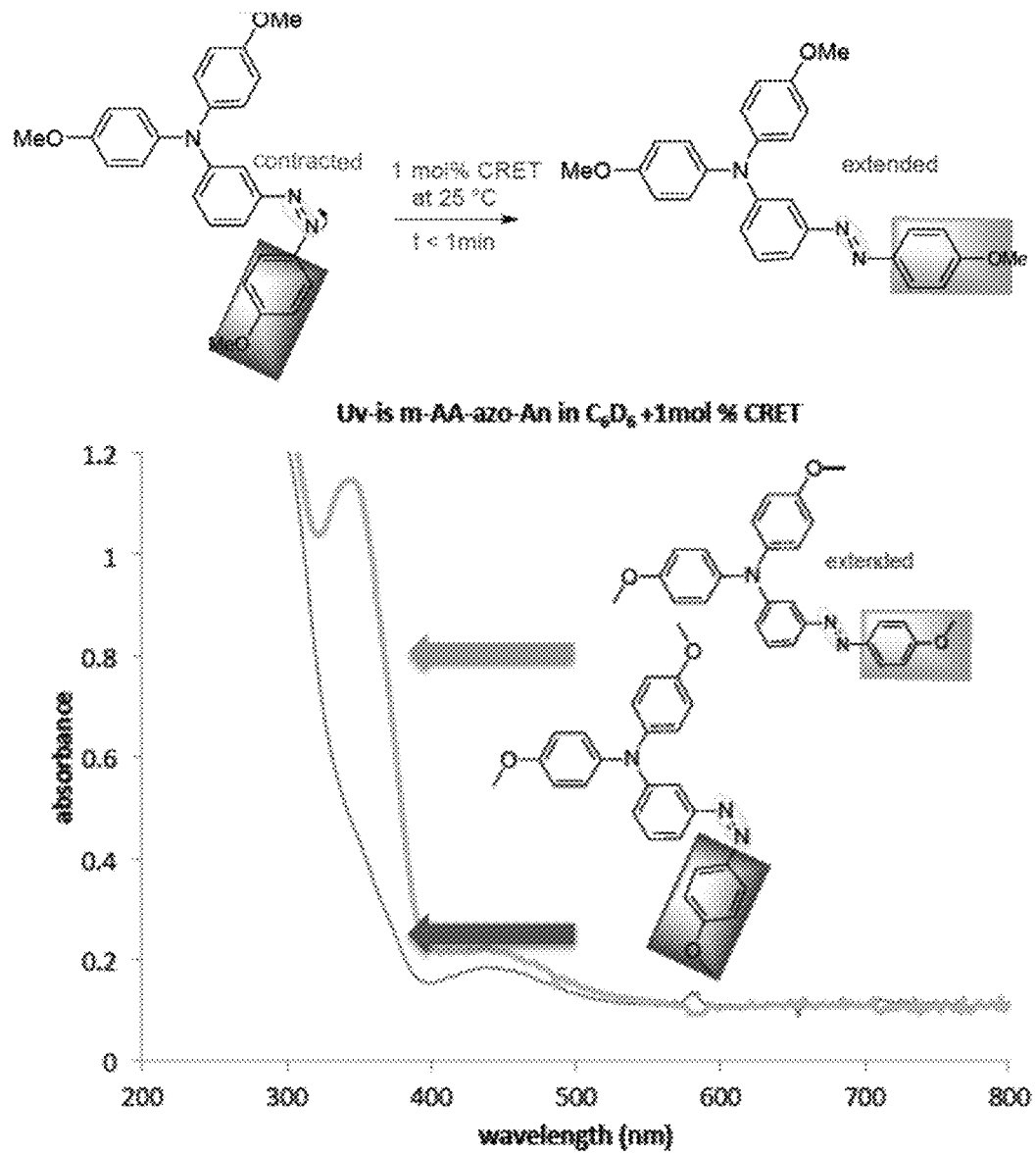
FIG. 17 shows the unfolding of the m-AA-N=N-An upon addition of CRET.

For the m-AA-N=N-An, conversion from the extended to the contracted state ("folding") was achieved with light of wavelengths longer than 345 nm, as shown in FIG. 15. The folding was also confirmed by observing changes in the H NMR signals of the methyl group (FIG. 16). Transition from the contracted state to the extended state ("unfolding") was achieved through the addition of a small amount of CRET (FIG. 17).

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A compound defined by Formula V:

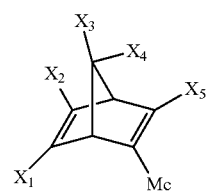

V wherein $X_1$-$X_5$ are independently chosen from hydrogen, halogen, $C_1$-$C_{24}$ alkyl, $C_2$-$C_{24}$ alkenyl, $C_2$-$C_{24}$ alkynyl, aryl, heteroaryl, alkoxyl, hydroxy, nitrile, nitro, —C(O)$R_1$, —$NR_1R_2$, —C(O)$NR_1R_2$;

wherein $R_1$ and $R_2$ are independently chosen from hydrogen, halogen, $C_1$-$C_{24}$ alkyl, $C_2$-$C_{24}$ alkenyl, $C_2$-$C_{24}$ alkynyl, $C_1$-$C_{24}$ aryl and $C_1$-$C_{24}$ heteroaryl, and wherein Mc is a metallocene.

2. The compound of claim 1, wherein the compound is defined by Formula VI:

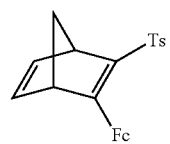

VI wherein Ts is a tosyl group, and wherein Fc is a ferrocene.

3. A method of activating a compound for a chemical reaction, comprising:
  a) providing the compound of claim 1; and
  b) oxidizing the redox auxiliary group that is bonded to the compound, thereby activating the compound of claim 1;
wherein the activated compound undergoes a chemical reaction to form a product, and
wherein the oxidation of the redox auxiliary group is reversible.

4. The method of claim 3, wherein the redox auxiliary group is oxidized photochemically, electrochemically, or a combination thereof.

5. The method of claim 3, wherein the oxidized redox auxiliary group exchanges an electron with a neutral redox auxiliary group to propagate electron transfer chain reaction to effect redox catalysis.

6. The method of claim 3, further comprising the step of removing the redox auxiliary group from the product.

7. The method of claim 3, wherein the reaction is an isomerization, a rearrangement, an electrocyclic reaction, a photoelectrochemical reaction, a thermal reaction, or a combination thereof.

\* \* \* \* \*